(12) United States Patent
Takeda et al.

(10) Patent No.: US 9,820,932 B2
(45) Date of Patent: *Nov. 21, 2017

(54) COSMETIC

(75) Inventors: Kyoichi Takeda, Chiba (JP); Yuki Kokeguchi, Chiba (JP); Mari Yoshida, Chiba (JP); Kiyoshi Maeno, Kanagawa (JP)

(73) Assignee: KOKYU ALCOHOL KOGYO CO., LTD., Narita (JP)

( * ) Notice: Subject to any disclaimer, the term of this patent is extended or adjusted under 35 U.S.C. 154(b) by 1694 days.

This patent is subject to a terminal disclaimer.

(21) Appl. No.: 10/590,151

(22) PCT Filed: Dec. 19, 2005

(86) PCT No.: PCT/JP2005/023287
§ 371 (c)(1),
(2), (4) Date: Aug. 21, 2006

(87) PCT Pub. No.: WO2006/095486
PCT Pub. Date: Sep. 14, 2006

(65) Prior Publication Data
US 2008/0188569 A1    Aug. 7, 2008

(30) Foreign Application Priority Data

Mar. 10, 2005    (JP) .................... 2005-110296

(51) Int. Cl.
| | | |
|---|---|---|
| *A61K 8/85* | (2006.01) | |
| *A61Q 19/00* | (2006.01) | |
| *C08G 63/20* | (2006.01) | |
| *A61Q 5/12* | (2006.01) | |
| *A61Q 5/04* | (2006.01) | |
| *A61Q 5/02* | (2006.01) | |
| *A61Q 1/08* | (2006.01) | |
| *A61Q 5/06* | (2006.01) | |
| *A61Q 17/04* | (2006.01) | |

(52) U.S. Cl.
CPC ................ *A61K 8/85* (2013.01); *A61Q 19/00* (2013.01); *A61Q 1/08* (2013.01); *A61Q 5/02* (2013.01); *A61Q 5/04* (2013.01); *A61Q 5/06* (2013.01); *A61Q 5/12* (2013.01); *A61Q 17/04* (2013.01); *C08G 63/20* (2013.01)

(58) Field of Classification Search
CPC ........ A61K 8/85; C08G 63/201; A61Q 19/00; A61Q 17/04; A61Q 5/12; A61Q 5/04; A61Q 5/02; A61Q 1/08; A61Q 5/06
See application file for complete search history.

(56) References Cited

U.S. PATENT DOCUMENTS 6,242,499 B1 * 6/2001 Gruning et al. ............. 514/785
6,800,275 B1   10/2004 O'Lenick, Jr.

FOREIGN PATENT DOCUMENTS

| | | |
|---|---|---|
| DE | 197 24 626 A1 | 12/1998 |
| EP | 0 899 617 A1 | 3/1999 |
| JP | A-62-205188 | 9/1987 |
| JP | A-8-165218 | 6/1996 |
| JP | A 2002-275020 | 9/2002 |
| JP | A 2003-226609 | 8/2003 |
| JP | A 2003-238332 | 8/2003 |
| JP | A 2004-256515 | 9/2004 |
| JP | A-2005-089487 | 4/2005 |
| JP | A 2005-132729 | 5/2005 |
| JP | A 2005-179377 | 7/2005 |

OTHER PUBLICATIONS

Solvay Chemicals International, Polyglycerols—General Overview, Revised Sep. 2008, Solvay Chemicals International, pp. 1-10.*

* cited by examiner

*Primary Examiner* — Trevor Love
(74) *Attorney, Agent, or Firm* — Oliff PLC

(57) ABSTRACT

The present invention relates to cosmetics comprising a hydroxyl compound obtained by the reaction of a di- or higher-valent alcohol with a monovalent carboxylic acid and dimer acid, characterized in that the hydroxyl compound is obtained by reacting diglycerin with isostearic acid, and then reacting the obtained ester compound with dimer acid, wherein a molar ratio among diglycerin, isostearic acid and dimer acid is in the range of 1.0:1.4 to 1.6:0.5 to 0.8. The present invention provides cosmetics comprising the hydroxyl compounds having a high hydroxyl value.

9 Claims, No Drawings

COSMETIC

FIELD OF THE INVENTION

The present invention relates to a cosmetic comprising a hydroxyl compound obtained by reacting diglycerin with isostearic acid and dimer acid.

BACKGROUND OF THE INVENTION

In the prior art, various ester compounds are known as an oily base used in cosmetics.

DEOS 19724626 discloses a sunscreen composition comprising a specific ultra-violet ray absorber of a triazine type and triglycerin dimerate isostearate. The ester compound is used as an emulsifier in W/O emulsion.

However, the ester compound is poor in compatibility with oily bases. Further it was difficult to obtain an ester compound in a homogeneous state in a reproducible manner because highly viscous substances formed in the condensation of triglycerin, which is a hexavalent alcohol, with isostearic acid and dimer acid.

Japanese Patent Application Laid-Open 2002-275020 discloses an oily base comprising an ester of at least one alcohol selected from the group consisting of divalent alcohols having 4 to 22 carbon atoms and tri- or higher-valent alcohols having 3 to 22 carbon atoms with one or two acids selected from the group consisting of dimer acids and hydrogenated dimer acids. As examples of the ester of divalent alcohols having 4 to 22 carbon atoms with dimer acid, mention is made of an ester compound of decane diol with dimer acid. As examples of the ester of tri- or higher-valent alcohols having 3 to 22 carbon atoms with dimer acid, mention is made of an ester compound of glycerin with dimer acid.

However, polymers with high molecular weight and cyclic polymers form in the preparation of the ester. Consequently, the viscosity of the reaction mixture in a reactor increases, so that it was difficult to obtain an ester compound in a homogeneous state in a reproducible manner.

Japanese Patent Application Laid-Open 2003-226609 discloses that an ester compound of one or two alcohols with dimer acid, or an ester compound of at least three alcohols with dimer acid is used as an oily base. There, use is made of higher alcohol, such as behenyl alcohol, stearyl alcohol, isostearyl alcohol, phytosterol. These ester compounds are called a wax type and their affinity to skin is weak.

Japanese Patent Application Laid-Open 2003-238332 discloses a cosmetic comprising an oligomer with a number average molecular weight of from 2,000 to 8,000 obtained by reaction of dimer acid with hardened castor oil. However, the oligomer is poor in compatibility with oily bases.

All of the ester compounds described in the afore-mentioned specifications are poor in compatibility or miscibility with various cosmetics and oily bases, so that their amounts in cosmetics are inevitably limited. Therefore, it was difficult to obtain cosmetics with good practical properties such as affinity, emollient property, and oily feeling.

Japanese Patent Application Laid-Open 2004-256515 discloses an oily base comprising (a) an ester obtained by esterification of an oligomeric ester of dimer acid and a di- or higher-valent alcohol with a monovalent alcohol and/or a monovalent carboxylic acid, or (b) an ester obtained by esterification of an oligomeric ester of dimer diol and a di- or higher-valent carboxylic acid with a monovalent alcohol and/or a monovalent carboxylic acid.

Processes for the preparation of ester (a) are disclosed wherein dimer acid is reacted with di- or higher-valent alcohol so as to obtain an oligomeric ester, and then the carboxyl groups and/or the hydroxyl groups of the oligomeric ester are esterified with a monovalent alcohol and/or monovalent carboxylic acid, or wherein dimer acid, di- or higher-valent alcohol, and a monovalent alcohol and/or a monovalent carboxylic acid are reacted at once for esterification. Processes for the preparation of ester (b) are disclosed wherein a dimer diol is reacted with a di- or higher-valent carboxylic acid so as to obtain an oligomeric ester, and then carboxylic groups and/or hydroxyl groups of the oligomeric ester are esterified with a monovalent alcohol and/or a carboxylic acid, or wherein a dimer diol, a di- or higher-valent carboxylic acid, and a monovalent alcohol and/or a monovalent carboxylic acid are reacted at once for esterfication.

In Examples 7 and 8, ester (a) was prepared by reacting an oligomeric ester from dimer acid with 1,10-decane diol or diethylene glycol, and then esterifying the oligomeric ester with a mixture of alcohol (behenyl alcohol and phytosterol). Ester (b) was prepared in Examples 1 to 5 and Example 9 by preparing an oligomeric ester from dimer acid and dimer diol, and then esterifying the oligomeric ester with isostearyl alcohol, behenyl alcohol, isostearic acid, or a mixture of alcohols (behenyl alcohol, isostearyl alcohol and phytosterol) and, in Example 6, by reacting dimer acid, dimer diol, and a mixture of alcohols at once for esterification. For ester (b), dimer diol was used as a raw material instead of di- or higher-valent alcohol.

The viscosities at 60 degrees C. of these esters range from 250 to 4,200 mPa·s, the weight average molecular weights range from 3,300 to 14,800, and the hydroxyl values range form 3.4 to 18.1 (Examples 1 to 9). Above all, the hydroxyl values are very low, so that the esters have drawbacks such as a poor moisturizing property and a poor emollient property.

Japanese Patent Application Laid-Open 2005-132729 discloses cosmetics comprising a mixed ester of aliphatic acids obtained by esterification of polyglycerin, dimer acid, and saturated aliphatic acid and/or unsaturated aliphatic acid. In Examples 1 and 2, diglycerin, dimer acid and carboxylic acid are placed in a reactor at once for esterification. There, the molar ratios among diglycerin, carboxylic acid and dimer acid are 1.0:2.74:0.51 and 1.0:2.22:1.02, respectively. The hydroxyl value, the viscosity at 60 degrees C., and the number average molecular weight of the obtained mixed ester of aliphatic acids are 5, 1,200 mPa·s, and 1,800 in Example 1 and 2.5, 7,200 mPa·s, and 5,500 in Example 2.

The hydroxyl values of the esters thus obtained are very low, as seen for the above-described esters.

SUMMARY OF THE INVENTION

Problems to be Solved by the Invention

The present invention is to provide a cosmetic comprising a hydroxyl compound having an appropriate hydroxyl value. Upon being formulated into cosmetics, the hydroxyl compound may provide not only a good emollient property and a good moisturizing property, but also good oily feeling, affinity, storage stability, and safety to skin.

Means to Solve the Problems

The inventors have found that a hydroxyl value of the hydroxyl compound may be adjusted to an appropriate range by reacting diglycerin, isostearic acid and dimer acid in a predetermined order and in predetermined amounts, and a cosmetic comprising the hydroxyl compound does not have the afore-mentioned problems. Thus the present invention has been completed.

Thus, the present invention is (1) a cosmetic comprising a hydroxyl compound obtained by reaction of a di- or higher-valent alcohol with a monovalent carboxylic acid and dimer acid, characterized in that the hydroxyl compound is obtained by reacting diglycerin with isostearic acid, and then reacting the obtained ester compound with dimer acid, and that a molar ratio among diglycerin, isostearic acid, and dimer acid is 1.0:1.4 to 1.6:0.5 to 0.8.

As described above, Japanese Patent Application Laid-Open 2004-256515 discloses an oily base comprising ester (a) and ester (b). As a raw material for the preparation of the ester (b), dimer diol is used. Diglycerin is not used. As a raw material for the preparation of the ester (a), dimer acid, a di- or higher-valent alcohol and a monovalent carboxylic acid are used. As the di- or higher-valent alcohol, many alcohols are disclosed, such as diglycerin. As the monovalent carboxylic acid, many carboxylic acids are disclosed, such as isostearic acid. However, the combination of diglycerin, isostearic acid and dimer acid is not described. In the Examples, as the di- or higher-valent alcohol, use was made of 1,10-decanediol or diethylene glycol, but not diglycerin. The hydroxyl values of the ester (a) and the ester (b) obtained in Example 10 were so low as 3.4 to 18.1. Japanese Patent Application Laid-Open 2004-256515 does disclose the amount of the monovalent alcohol and/or the monovalent carboxylic acid relative to the amount of the di- or higher-valent alcohol.

In the present invention, diglycerin and isostearic acid are selected from various known raw materials for ester compounds and reacted in the predetermined order and in the predetermined amounts to successfully obtain the hydroxyl compound with an appropriate hydroxyl value, which is not obtained in the invention of Japanese Patent Application Laid-Open 2004-256515. The hydroxyl compound has an appropriate hydroxyl value as well as a high viscosity and good compatibility or miscibility with various oily bases used in cosmetics.

As preferred embodiments of the present invention, mention may be made of:

(2) the cosmetic according to the above (1), wherein the molar ratio among diglycerin, isostearic aid, and dimer acid is 1.0:1.45 to 1.55:0.55 to 0.75;

(3) the cosmetic according to the above (1), wherein the molar ratio among diglycerin, isostearic aid, and dimer acid is 1.0:1.47 to 1.53:0.6 to 0.7;

(4) the cosmetic according to the above (1) to (3), wherein the hydroxyl value of the hydroxyl compound is in a range of from 30 to 80;

(5) the cosmetic according to the above (1) to (3), wherein the hydroxyl value of the hydroxyl compound is in a range of from 40 to 70;

(6) the cosmetic according to the above (1) to (5), wherein the viscosity at 60 degrees C. of the hydroxyl compound is in a range of from 2,000 to 15,000 mPa·s;

(7) the cosmetic according to the above (1) to (5), wherein a viscosity at 60 degrees C. of the hydroxyl compound is in a range of from 2,500 to 10,000 mPa·s;

(8) the cosmetic according to the above (1) to (5), wherein a viscosity at 60 degrees C. of the hydroxyl compound is in a range of from 3,000 to 8,000 mPa·s;

(9) the cosmetic according to the above (1) to (8), wherein a number average molecular weight of the hydroxyl compound is in a range of from 2,000 to 7,000; and

(10) the cosmetic according to the above (1) to (8), wherein a number average molecular weight of the hydroxyl compound is in a range of from 3,000 to 6,000.

Effects of the Invention

The hydroxyl compound contained in the cosmetics of the present invention has an appropriate hydroxyl value. Accordingly, the cosmetic of the present invention has a good emollient property and a good moisturizing property. Additionally the hydroxyl compound has appropriate viscosity and number average molecular weight. Accordingly, it is possible to obtain cosmetics having good practical properties such as affinity and oily feel, storage stability, and safety to skin. The compound may be used in various types of cosmetics by changing its hydroxyl value, viscosity, and number average molecular weight as required. For highly viscous cosmetics or solid cosmetics, the hydroxyl compound of the present invention can reduce an amount of plant wax, such as solid paraffin, candelilla wax, carnauba wax, and hardened castor oil.

DESCRIPTION OF THE PREFERRED EMBODIMENTS

Diglycerin, isostearic acid and dimer acid used in the preparation of the hydroxyl compound of the present invention are all known compounds. It is possible to use commercially available ones. As diglycerin, for instance, use may be made of "K COL II", trademark, from ADEKA Co., LTD., "diglycerin 801", trademark, from Sakamoto Yakuhin Kogyo Co., Ltd., and "Diglycerol", trademark, from Solvay. As isostearic acid, use may be made of, for instance, "isostearic acid EX", trademark, from Kokyu Alcohol Kogyo Co., Ltd., "PRISORINE 3505", trademark, from Uniqema Co., Ltd., "Emersol 874", trademark, from Cognis, and "Century 1115" and "Century 1107", trademarks, from Arizona Chemical. As dimer acid, use may be made of, for instance, those described in the above-mentioned patent documents. As commercially available ones, mention may be made of, for instance, "PRIPOL 1009", trademark, from Uniqema, "Empol 1062" and "Empol 1008", trademarks, from Cognis, and "Unidyme 14" and "Unidyme 14R", trademarks, from Arizona Chemical. Here, dimer acid is a cyclic dicarboxylic acid obtained by polymerizing two molecules of unsaturated aliphatic acid, such as oleic acid and linoleic acid, via the Diels-Alder reaction. The afore-mentioned commercially available dimer acid is one obtained by hydrogenation and distillation of a Diels-Alder product, and is also referred to as hydrogenated dimer acid.

The hydroxyl compound of the present invention is prepared in a two-step process comprising a first step wherein diglycerin is reacted with isostearic acid, and a second step wherein the ester compound thus obtained is reacted with dimer acid. In the first step, isostearic acid binds preferentially to the hydroxyl group at position 1, primary hydroxyl group, of the diglycerin due to the reactivity difference among the hydroxyl groups of the diglycerin. Accordingly, the obtained mono-ester and di-ester are esterified more at position 1 of the diglycerin. Upon further esterifying these with dimer acid, more hydroxyl compound has a coupled structure wherein the dimer acid binds to the remaining hydroxyl group at position 2, secondary hydroxyl group. With this process, it is possible to control properties of the hydroxyl compound, such as viscosity, number average molecular weight, and hydroxyl value, more properly than with the one-step process wherein diglycerin, isostearic acid and dimer acid are reacted simultaneously. It is also possible to reduce variation in properties, which occur among lots of raw materials and types and/or dimensions of a reactor.

An example of the two-step process is as follows: in the first step, diglycerin and isostearic acid are placed in a reactor and the temperature is raised gradually preferably to a temperature of from 100 to 250 degrees C., and more preferably from 180 to 240 degrees C. while distilling off the produced water. The reaction mixture is retained at the temperature until no water is distilled off any more. The retention time is preferably 2 to 50 hours, more preferably 3 to 40 hours, and further more preferably 4 to 30 hours. In the second step, the ester compound obtained in the first step and dimer acid are placed in a reactor and, then, reacted under the same conditions as in the first step. In the first step, the reaction is performed so that the hydroxyl value of the ester of diglycerin with isostearic acid is preferably 150 to 330. In actual operations, an acid value of the ester compound is monitored and adjusted preferably to at most 5.0, more preferably at most 3.0. The acid value can be determined accurately in a shorter time, so that reaction is controlled more easily with the acid value. The acid value is determined according to the Cosmetics Raw Material Standards. By controlling the hydroxyl or acid value in this way, it is possible to easily control the viscosity and the hydroxyl value of the desired hydroxyl compound in the reaction of the ester compound obtained in the first step with a predetermined amount of dimer acid in the second step.

The reaction described above is performed preferably in the absence of a solvent and a catalyst, whereby it is possible to obtain a hydroxyl compound in a homogeneous state in a reproducible manner. The hydroxyl compound obtained is not accompanied with a solvent or catalyst, so that a cosmetic containing the compound is safer to skin. Meanwhile, a catalyst and/or a solvent may be used, whereby, reaction time may be shortened. As examples of the catalyst, mention may be made of sodium hydroxide, para-toluene sulfonic acid, sulfuric acid, hydrochloric acid, methanesulfonic acid, boron trifluoride, and hydrogen fluoride. As examples of the solvent, mention may be made of benzene and toluene.

In manufacturing the hydroxyl compound, diglycerin and isostearic acid are used in a molar ratio of 1.0:1.4 to 1.6, preferably 1.0:1.45 to 1.55, and more preferably 1.0:1.47 to 1.53. If the proportion of isostearic acid is below the afore-mentioned lower limit, the hydroxyl value of the hydroxyl compound exceeds the range of the present invention. If the proportion exceeds the afore-mentioned upper limit, the hydroxyl value is below the range of the present invention. By controlling the ratio between the two compounds in the above-described range, problems can be avoided, such as, for instance, separation of diglycerin after the reaction due to the existence of the unreacted diglycerin, and formation of undesired by-products such as diester and triester. Diglycerin and dimer acid are used in a molar ratio of 1.0:0.5 to 0.8, preferably 1.0:0.55 to 0.75, and more preferably 1.0:0.6 to 0.7. If the ratio of the dimer acid is below the afore-mentioned lower limit, the degree of polymerization of the hydroxyl compound is not enough to result in an oligomer with low viscosity. If the ratio exceeds the afore-mentioned upper limit, the degree of polymerization of the hydroxyl compound is significantly large to cause gelation in a reactor, so that the reaction may not be complete.

The upper limit of the hydroxyl value of the obtained hydroxyl compound is 80, preferably 75, and more preferably 70 and the lower limit is 30, preferably 35, and more preferably 40. If the hydroxyl value exceeds the afore-mentioned upper limit, the compound is less compatible with oily bases. If the hydroxyl value is lower than the afore-mentioned lower limit, the compound is poor in the moisturizing property and the emollient property.

The upper limit of the viscosity at 60 degrees C. of the hydroxyl compound is preferably 15,000 mPa·s, preferably 10,000 mPa·s, and more preferably 8,000 mPa·s. The lower limit is preferably 2,000 mPa·s, more preferably 2,500 mPa·s, and more preferably 3,000 mPa·s. Above the afore-mentioned upper limit, handling of it is difficult. Below the lower limit, affinity is too poor for cosmetics.

The upper limit of the number average molecular weight of the hydroxyl compound is preferably 7,000, more preferably 6,000, and more preferably 5,000 and the lower limit is 2,000, preferably 2,500, and more preferably 3,000. Above the afore-mentioned upper limit, handling of it is difficult. Below the lower limit, affinity is too poor for cosmetics.

The content of the hydroxyl compound of the present invention depends on the type of the cosmetics and ranges from 0.5 to 70% by mass, more preferably from 1.0 to 60% by mass, and more preferably from 1.5 to 50% by mass.

In the following Examples, the present invention will be described in detail, but not limited thereto.

EXAMPLES

Preparation Examples

The substances used in the Preparation Examples and the Comparative Preparation Examples were as follows, unless otherwise stated;
Diglycerin: "K COL II", trademark, from ADEKA Co. Ltd.
Isostearic acid: "isostearic acid EX", trademark, from Kokyu Alcohol Kogyo Co. Ltd., and
Dimer acid; "PRIPOL 1009", trademark, from Uniqema.

Viscosity and number average molecular weight of the hydroxyl compounds were determined as follow;
Viscosity: determined by Brookfield Viscometer DV-II+ (Spindle No. 3, 12 rpm, 60 degrees C.)
Number average molecular weight: determined from distribution of molecular weight relative to polystyrene via GPC, gel permeation chromatography;
  Instrument: SC-8010 from Tosho Corporation;
  Column: each two Shodex KF-800D and KF-805L;
  Eluent: THF;
  Temperature: 40 degrees C. in a temperature-controlled bath for column
  Flow rate: 11.0 mL/min.;
  Injection volume: 100 μL, about 0.2% (weight/volume);
  Solubility: completely dissolved;
  Detector: Refractive Index Detector (RI)
Hydroxyl value: determined in accordance with "Cosmetics Raw Material Standard 24, Method for the Determination of a Hydroxyl Value"; and
Acid value: determined in accordance with "Cosmetics Raw Material Standard 18, Method for the Determination of an Acid Value".

Preparation Example 1

In a four-neck 1000 mL flask equipped with a stirrer, a thermometer, a nitrogen gas inlet tube, and a Dean-Stark condenser with a water measuring trap were placed 133 g (0.8 mole) of diglycerin, 341 g (1.2 moles) of isostearic acid, 160 mL of toluene as a solvent, and 0.28 g of sodium hydroxide as catalyst. Then, the reaction mixture was heated to 200 degrees C. under a flow of nitrogen gas at a rate of 10 mL/min. At the temperature, the reaction took place while distilling off the produced water with the solvent azeotropically. When the distillation-off of water subsided, the temperature was raised to 215 degrees C. to further continue the reaction. When the distillation-off of water stopped, the reaction was terminated. It took about 5 hours from the start of the reaction to this point. Diglycerin isostearate was obtained as a pale yellow viscous oil in an amount of 452 g (hydroxyl value: 229, acid value: 0.8).

Next, the above-described apparatus was charged with 450 g of the obtained diglycerin isostearate and 224 g (0.40 mole) of dimer acid. Then, under a flow of nitrogen gas at a rate of 50 mL/min., the reaction took place while distillation-off the produced water at a temperature of 200 degrees C. and then at 215 degrees C. as described above. When the distillation-off of water stopped, the reaction was terminated. It took about 5 hours from the start of the reaction to this point.

To the obtained product, 350 mL of toluene as a solvent was added to decrease the viscosity and then 17 g of Galleon Earth, activated clay from Mizusawa Industrial Chemicals Ltd. was added. Then the reaction mixture was stirred at about 80 degrees C. for 30 min. and then filtered to remove the catalyst which was adsorbed on the activated clay. Using a rotary evaporator, the solvent was removed from the obtained filtrate to obtain 611 g of a hydroxyl compound as a pale yellow viscous oil.

The molar ratio among diglycerin, isostearic acid and dimer acid used in the reaction was 1.0:1.5:0.5.

Preparation Example 2

In this Preparation Example, no catalysts were used. The same apparatus as that used in Preparation Example 1 was charged with 133 g (0.8 mole) of diglycerin and 341 g (1.2 moles) of isostearic acid. Then, the reaction mixture was heated to 200 degrees C. under a flow of nitrogen gas at a rate of 50 mL/min. At the temperature, the reaction took place while distilling off the produced water together with the solvent azeotropically. When the water distillation subsided, the temperature was raised to 220 degrees C. to further continue the reaction. When the distillation-off of water stopped, the reaction was terminated. It took about 8 hours from the start of the reaction to this point. Diglycerin isostearate was obtained as a pale yellow viscous oil in an amount of 452 g (hydroxyl value: 232, acid value: 0.6).

Next, the above-described apparatus was charged with 450 g of the obtained diglycerin isostearate and 224 g (0.40 mole) of dimer acid. Then, under a flow of nitrogen gas at a rate of 50 mL/min., the reaction took place while distilling off the produced water at a temperature of 200 degrees C. and 220 degrees C. as described above. When the distillation-off of water stopped, the reaction was terminated. It took about 8 hours from the start of the reaction to this point. 662 g of a hydroxyl compound was obtained as a pale yellow viscous oil.

The molar ratio among the diglycerin, isostearic acid, and dimer acid used in the reaction was 1.0:1.5:0.5.

Preparation Example 3

The procedures of Preparation Example 2 were repeated, except that the amount of dimer acid used in the second step was changed to 291 g (0.52 mole). 724 g of a hydroxyl compound was obtained as a pale yellow viscous oil. The molar ratio among the diglycerin, isostearic acid and dimer acid used in the reaction was 1.0:1.5:0.65.

Preparation Example 4

To the same apparatus as that used in Preparation Example 1 were added 300 g of RISOREX PGIS21, trademark for diglycerin isostearate from Kokyu Alcohol Kogyo Co. Ltd. (acid value: 0.5; and hydroxyl value: 152.7), 194.0 g (0.34 mole) of dimer acid, 0.15 g of sodium hydroxide, and 130 mL of toluene. Then, under a flow of nitrogen gas at a rate of 10 mL/min., the reaction took place at 215 degrees C. while distilling off the water produced. When the distillation-off of water stopped, the reaction was terminated. The reaction time was about 6 hours. According to the same procedures as those in Preparation Example 1, the catalyst was removed from the reaction mixture to obtain 454 g of a hydroxyl compound as a pale yellow viscous oil.

The molar ratio between the diglycerin isostearate and dimer acid used in the reaction was 1.0:0.65. The ratio corresponded to a molar ratio among diglycerin, isostearic acid and dimer acid of 1.0:1.5:0.65 in terms of.

Preparation Example 5

The same procedures as in Preparation Example 1 were repeated, except that the amount of isostearic acid in the first step was changed to 365 g (1.28 moles) and that of dimer acid in the second step was changed to 314 g (0.56 mole). 731 g of a hydroxyl compound was obtained as a pale yellow highly viscous oil.

The molar ratio among the diglycerin, isostearic acid, and dimer acid used in the reaction was 1.0:1.6:0.7.

Preparation Example 6

The same procedures as in Preparation Example 1 were repeated, except that the amount of dimer acid used in the second step was changed to 358 g (0.64 mole). 729 g of a hydroxyl compound was obtained as a pale yellow highly viscous oil.

The molar ratio among the diglycerin, isostearic acid, and dimer acid used in the reaction was 1.0:1.5:0.8.

Preparation Example 7

The same procedures as in Preparation Example 1 were repeated, except that the amount of isostearic acid in the first step was changed to 319 g (1.12 moles) and the amount of dimer acid in the second step was changed to 224 g (0.40 mole). 621 g of a hydroxyl compound was obtained as a pale yellow highly viscous oil.

The molar ratio among the diglycerin, isostearic acid, and dimer acid used in the reaction was 1.0:1.4:0.5

Comparative Preparation Example 1

In this Comparative Preparation Example, a hydroxyl compound was prepared according to the process described in DEOS 19724626. To the same apparatus as that used in Example 1 were added 120 g (0.5 mole) of triglycerin and 285 g (1.0 mole) of isostearic acid. The reaction in the first step took place as described in Example 2. 387 g of triglycerin isostearate was obtained.

Then 387 g of the obtained triglycerin isostearate and 56 g (0.10 mole) of dimer acid were placed in the apparatus. The reaction in the second step took place as described in Preparation Example 2. 483 g of a hydroxyl compound was obtained as a pale yellow highly viscous oil.

Comparative Preparation Example 2

In this Comparative Preparation Example, a hydroxyl compound was prepared according to the process described in Japanese Patent Application Laid-Open 2002-275020. To a 500 mL reactor equipped with a stirrer, a thermometer, and a gas inlet tube were added 175.0 g (0.304 mole) of dimer acid and 55.98 g (0.608 mole) of glycerin, followed by heating to 220 degrees C. under a nitrogen flow. At the temperature the reaction took place while distilling off the produced water azeotropically together with the solvent. When the distillation of produced water subsided, the temperature was raised to 240 degrees C. and the reaction was continued further. When the distillation-off of water stopped, the reaction was terminated. It took about 3 hours from the start of the reaction to this point. Then the unreacted glycerin was removed by distillation under reduced pressure to obtain 187.1 g of glycerin ester of dimer acid as a pale yellow highly viscous oil.

Comparative Preparation Example 3

In this Comparative Preparation Example, a hydroxyl compound was prepared according to the process described in Japanese Patent Application Laid-Open 2003-238332. In a 5 L four-neck glass flask equipped with a stirrer, a thermometer, a reflux condenser, and a nitrogen gas feeding nozzle were added 2000 g (1.92 moles) of "Himako P", trademark for hydrogenated castor oil from Kawaken Fine Chemicals Co. Ltd., 549.6 g (0.96 mole) of dimer acid, 200 mL of toluene, and 8.2 g of para-toluene sulfonic acid. Then the mixture was heated to 220 degrees C. under a nitrogen flow. The reaction took place until the acid value became 2 or less. Then, the mixture was cooled to 80 degrees C., 1000 mL of toluene was added, and the mixture was washed with warm water to remove the catalyst. Then the toluene was removed by distillation under reduced pressure to obtain 2515 g of an oligomer of hydrogenated castor oil with dimer acid.

Comparative Preparation Example 4

In this comparative preparation example, a hydroxyl compound was prepared according to the process of Japanese Patent Application Laid-Open 2004-256515 for preparing ester (b). To a 1 L reactor equipped with a stirrer, a thermometer, and a gas inlet tube were added 200 g (0.348 mole) of dimer acid, 137 g (0.253 mole) of PRIPOL2033, trademark for dimer diol from Uniqema, 137 g of heptane, and 1.3 g of para-toluene sulfonic acid. Then the mixture was heated to a range of from 100 to 110 degrees C. under a nitrogen flow. The reaction took place for 3 hours while distilling off the produced water to obtain an oligomeric ester of dimer acid with dimer diol.

To the obtained oligomeric ester of dimer acid with dimer diol was added 47.9 g (0.181 mole) of Speziol C18 ISOC, trademark for isostearyl alcohol from Cognis. Then the reaction mixture was heated to a range of 105 to 110 degrees C. The reaction took place for 5 hours under distilling off the produced water. After cooled, the remaining catalyst was removed by washing with water and then the heptane as a solvent was recovered. 355 g of the desired ester was obtained as a pale yellow highly viscous oil.

Comparative Preparation Example 5

In this comparative preparation example, the amount of the dimer acid used exceeded the range of the present invention. The same procedures as those in Preparation Example 1 were repeated, except that 449 g (0.80 mole) of dimer acid was placed in the reactor. The reaction took place under distillation-off of the produced water. The viscosity rose rapidly before the distillation-off of the produced water would stop in the second step, namely 2 hours after the start of the reaction, so that the stirring was difficult. Therefore the reaction was terminated. 885 g of a hydroxyl compound was obtained as a yellow gummy product. It was difficult to determine the properties of the hydroxyl compound to obtain values with high accuracy.

The molar ratio among the glycerin, isostearic acid, and dimer acid used in the reaction was 1.0:1.5:1.0.

Comparative Preparation Example 6

In this comparative preparation example, the amount of the dimer acid used was below the range of the present invention. The same procedures as those in Preparation Example 1 were repeated, except that 224 g (0.40 mole) of dimer acid was placed in the reactor. The reaction was terminated when the distillation-off of the produced water stopped. 656 g of a hydroxyl compound was obtained as a pale yellow highly viscous oil.

The molar ratio among the glycerin, isostearic acid, and dimer acid used in the reaction was 1.0:1.5:0.4.

Comparative Preparation Example 7

In this comparative preparation example, the amount of the isostearic acid used was below the range of the present invention. The same procedures as those in Preparation Example 1 were repeated, except that 272.8 g (0.96 mole) of isostearic acid was used. On cooling the product to about 100 degrees C., it turned gel-like. The hydroxyl value of the product was 126 and the acid value was 0.1. The molar ratio between the diglycerin and isostearic acid used in the reaction was 1.0:1.2.

On cooling the product to 25 degrees C., it separated into two phases. The lower phase was taken to recover 8.5 g of highly viscous liquid. The analysis of this showed that this was unreacted diglycerin. The total amount of the unreacted diglycerin including the diglycerin dissolved in the upper phase was 23.7 g, which corresponded to 14% of the amount placed in the reactor. When the amount of the isostearic acid used was low, the reaction did not finish, so that the reaction yielded only a product containing a quantity of unreacted diglycerin. On reacting the product with dimer acid, the reaction yielded a product containing a quantity of condensate of diglycerin with dimer acid as an impurity. The desired hydroxyl compound was scarcely obtained.

Comparative Preparation Example 8

In this comparative preparation example, the amount of the isostearic acid used exceeded the range of the present invention. The same procedures as those in Preparation Example 1 were repeated, except that 409.2 g (1.44 moles) of isostearic acid was used. Diglycerin isostearate (hydroxyl value: 166, acid value: 1.1) was obtained as a pale yellow viscous oil. No separation or deposition of unreacted diglycerin was observed in the product.

To a 2 L flask, 500 g of the product was transferred. 219 g (0.39 mole) of dimer acid was added and the reaction was carried out in the same procedures while distilling off the produced water. When the distillation-off of the produced water stopped, the reaction was terminated.

To the obtained product, 400 ml of toluene, solvent, was added to reduce the viscosity and then 22 g of Galleon Earth, active white clay, from Mizusawa Chemicals Co. Ltd., was added. The mixture was stirred at 80 degrees C. for 30 min. and the catalyst which was adsorbed on the white clay was filtered off. Using a rotary evaporator, the solvent was removed from the obtained filtrate to obtain 705 g of a hydroxyl compound as a pale yellow highly viscous oil.

The molar ratio among the diglycerin, isostearic acid, and dimer acid used in the reaction was 1.0 to 1.8 to 0.5

Comparative Preparation Example 9

In this comparative preparation example, diglycerin was reacted first with dimer acid according to the process described in Japanese Patent Application Laid-Open 2004-256515. To the same apparatus as in Preparation Example 1 were added 133 g (0.8 mole) of diglycerin, 224 g (0.4 mole) of dimer acid, 160 mL of toluene as a solvent, and 0.28 g of sodium hydroxide as catalyst. Then the reaction took place as described in Preparation Example 1. On cooling the obtained product to about 100 degrees C., it turned gel-like. The acid value of the product was 3.8.

To the product, 341 g (1.2 moles) of isostearic acid was added. Then the reaction took place as described above. The gel-like substance still remained in the obtained product so that the product was not homogeneous. The acid value of the product was as high as 38. Thus, the reaction was not complete.

Properties of each substance obtained in the Preparation Examples and the Comparative Preparation Examples are shown in Table 1.

reaction time could be shortened compared to Preparation Example 2 where no catalyst was used. In Preparation Example 3, the reaction was carried out as described in Preparation Example 2, except that the amount of dimer acid was increased. The hydroxyl value decreased and the viscosity and the number average molecular weight increased. In Preparation Example 4, the reaction was carried out as described in Preparation Example 3, except that commercially available diglyceryl isostearate was used and a catalyst was used. Almost the same properties were obtained as in Preparation Example 3. In Preparation Example 5, the reaction was carried out as described in Preparation Example 1, except that the amounts of isostearic acid and dimer acid used were increased. The hydroxyl value decreased significantly, and the viscosity and the number average molecular weight increased greatly. The obtained hydroxyl compound demonstrated the effects of the present invention. In Preparation Example 6, the reaction was carried as described in Preparation Example 1, except that the amount of dimer acid used was increased. The viscosity and the number average molecular weight increased greatly. In Preparation Example 7, the amount of isostearic acid used was decreased. Almost the same properties as in Preparation Example 1 were obtained.

In Comparative Preparation Example 1, the hydroxyl compound was prepared according the process described in DEOS 19724626. The obtained hydroxyl compound had a very high hydroxyl value. In Comparative Preparation Example 2, the hydroxyl compound was prepared according to the process described in Japanese Patent Application Laid-Open 2002-275020. The obtained hydroxyl compound had a very large hydroxyl value and a very large viscosity. In Comparative Preparation Example 3, the hydroxyl compound was prepared according to the process described in Japanese Patent Application Laid-Open 2003-238332. The hydroxyl value was large. In Comparative Preparation Example 4, the hydroxyl compound was were prepared according the process described in Japanese Patent Appli-

TABLE 1

| | Molar ratio | | | Viscosity in | Number average | | |
|---|---|---|---|---|---|---|---|
| | Diglycerin | Isostearic acid | Dimer acid | mPa · s at 60° C. | molecular weight | Hydroxyl value | Acid value |
| Prep. Ex. 1 | 1.00 | 1.50 | 0.50 | 2500 | 2600 | 70.1 | 1.8 |
| Prep. Ex. 2 | 1.00 | 1.50 | 0.50 | 3100 | 3100 | 72.5 | 2.1 |
| Prep. Ex. 3 | 1.00 | 1.50 | 0.65 | 4600 | 4600 | 54.3 | 2.4 |
| Prep. Ex. 4 | 1.00 | 1.50 | 0.65 | 3900 | 4400 | 53.5 | 1.6 |
| Prep. Ex. 5 | 1.00 | 1.60 | 0.70 | 8500 | 5100 | 38.6 | 2.7 |
| Prep. Ex. 6 | 1.00 | 1.50 | 0.80 | 11500 | 6600 | 40.5 | 2.2 |
| Prep. Ex. 7 | 1.00 | 1.40 | 0.50 | 2100 | 2300 | 79.1 | 1.9 |
| Com. Prep. Ex. 1 | — | — | — | 14900 | 2000 | 110.3 | 3.4 |
| Com. Prep. Ex. 2 | — | — | — | 27000 | 2300 | 158.7 | 0.0 |
| Com. Prep. Ex. 3 | — | — | — | 4400 | 3600 | 81.7 | 0.7 |
| Com. Prep. Ex. 4 | — | — | — | 4200 | 4500 | 3.4 | 0.9 |
| Com. Prep. Ex. 5 | 1.00 | 1.50 | 1.00 | 42000 | —*1 | —*1 | —*1 |
| Com. Prep. Ex. 6 | 1.00 | 1.50 | 0.40 | 1500 | 1800 | 93.0 | 2.4 |
| Com. Prep. Ex. 7*2 | 1.00 | 1.20 | | — | — | — | — |
| Com. Prep. Ex. 8 | 1.00 | 1.80 | 0.50 | 980 | 3300 | 24.8 | 2.8 |
| Com. Prep. Ex. 9 | 1.00 | 1.50 | 0.50 | —*1 | —*1 | —*1 | 38.0 |

*1 incapable of being determined
*2 the desired compound was not obtained
Prep. Ex.: Preparation Example
Com. Prep. Ex.: Comparative Preparation Example In Preparation Examples 1 to 7, the hydroxyl compounds of the present invention were prepared. All of the hydroxyl compounds obtained had an appropriate hydroxyl value. In Preparation Example 1, a catalyst was used. Here, the cation Laid-Open 2004-256515. The hydroxyl value of the obtained hydroxyl compounds was very small. In Comparative Preparation Example 5, the procedures of Preparation 1 were repeated, except that the amount of dimer acid used exceeded the range of the present invention. The hydroxyl compound having a very high viscosity was obtained, so that neither hydroxyl value nor number average molecular weight could be determined. In Comparative Preparation Example 6, the procedures of Preparation 1 were repeated, except that the amount of dimer acid used was below the range of the present invention. The obtained hydroxyl compound had a very low viscosity and a number average molecular weight. Meanwhile, the hydroxyl value was high. In Comparative Preparation Example 7, the procedures of Preparation 1 were repeated, except that the amount of isostearic acid used was below the range of the present invention. No desired hydroxyl compound was obtained. In Comparative Preparation Example 8, the procedures of Preparation 1 were repeated, except that the amount of isostearic acid used exceeded the range of the present invention. The hydroxyl value, the viscosity, and the number average molecular weight of the obtained hydroxyl compound was very low. In Comparative Preparation Example 9, diglycerin was reacted first with dimer acid according to the process described in Japanese Patent Application Laid-Open 2004-256515. The reaction was not complete and no desired hydroxyl compound was obtained.

For each of the compounds obtained in the Preparation Examples and the Comparative Preparation Examples, the compatibility, water-holding property, and solubility with polyamide resins are as follows.

Compatibility Test

The hydroxyl compounds obtained in the Preparation Examples and the Comparative Preparation Examples were used as a sample. The hydroxyl compound (10% by mass) was dissolved in various oily bases (90% by mass), which are generally used in cosmetics, under stirring in a water bath at a temperature of from 80 to 90 degrees C. for about 30 min. Then the mixture was cooled to 50 degrees C. under stirring and kept in a temperature-controlled room of 25 degrees C. One week later, the state was visually evaluated. The evaluation was made as follows: when the hydroxyl compound was compatible, it was rated as "G"; when turbidity or slight separation state was observed, it was rated as "M"; and when complete separation was observed, it was rated as "B". The results are shown in Table 2.

TABLE 2

| Oily base | Prep. Ex. 1 | Prep. Ex. 2 | Prep. Ex. 3 | Prep. Ex. 4 | Prep. Ex. 5 | Prep. Ex. 6 | Prep. Ex. 7 | Com. Prep. Ex. 1 | Com. Prep. Ex. 2 |
|---|---|---|---|---|---|---|---|---|---|
| Polyglyceryl-2 triisostearate | G | G | G | G | G | G | G | G | G |
| Diisostearyl malate | G | G | G | G | G | G | G | G | G |
| Isotridecyl isononanoate | G | G | G | G | G | G | G | G | M |
| Cetyl ethylhexanoate | G | G | G | G | G | G | M | G | M |
| Hexyldecyl ethylhexanoate | G | G | G | G | G | G | M | G | M |
| Neopentyl glycol diethylhexanoate | G | G | G | G | G | G | M | M | B |
| Tiethylhexanoin | G | G | G | G | G | G | M | M | B |
| Trimethylolpropane triethylhexanoate | G | G | G | G | G | G | M | M | B |
| Pentaerythrityl tetraethylhexanoate | G | G | G | G | G | G | M | M | B |
| Pentaerythrityl tetraisostearate | G | G | G | G | G | G | M | B | M |

| Oily base | Com. Prep. Ex. 3 | Com. Prep. Ex. 4 | Com. Prep. Ex. 5 | Com. Prep. Ex. 6 | Com. Prep. Ex. 7 | Com. Prep. Ex. 8 | Com. Prep. Ex. 9 |
|---|---|---|---|---|---|---|---|
| Polyglyceryl-2 triisostearate | M | G | B | G | — | G | — |
| Diisostearyl malate | M | G | B | G | — | G | — |
| Isotridecyl isononanoate | B | G | B | M | — | G | — |
| Cetyl ethylhexanoate | B | G | B | M | — | G | — |
| Hexyldecyl ethylhexanoate | B | G | B | B | — | G | — |
| Neopentyl glycol diethylhexanoate | B | G | B | B | — | G | — |
| Tiethylhexanoin | B | G | B | B | — | G | — |
| Trimethylolpropane triethylhexanoate | B | M | B | B | — | G | — |
| Pentaerythrityl tetraethylhexanoate | B | M | B | B | — | G | — |
| Pentaerythrityl tetraisostearate | B | M | B | B | — | G | — |

Prep Ex.: Preparation Example
Comp. Prep. Ex.: Comparative Preparation Example

Water-Holding (Moisturizing) Property Test

The hydroxyl compounds obtained in the Preparation Examples and the Comparative Preparation Examples were used as a sample. 10 g of the hydroxyl compound at 35 degrees C. was weighed into a container kept at 35 degrees C. and purified water of 35 degrees C. was added dropwise and kneaded until no more water could be mixed in homogeneously. The mixture was kept at 25 degrees C. for 24 hours and then the amount of water that was separated from the mixture was weighed. The water-holding property in % was expressed as a ratio of the amount of the purified water finally contained in the mixture to the weight of the esterified compound at the starting point (10 g). The hydroxyl compound with the water-holding property of at least 300% was rated as "G"; that with at least 200% and less than 300%, "M"; and that with less than 200%, "B". The results are shown in Table 3.

TABLE 3

| Prep. Ex. 1 | Prep. Ex. 2 | Prep. Ex. 3 | Prep. Ex. 4 | Prep. Ex. 5 | Prep. Ex. 6 |
|---|---|---|---|---|---|
| G | G | G | G | G | G |

| Prep. Ex. 7 | Com. Prep. Ex. 1 | Com. Prep. Ex. 2 | Com. Prep. Ex. 3 | Com. Prep. Ex. 4 | Com. Prep. Ex. 5 |
|---|---|---|---|---|---|
| G | M | G | M | B | B |

| Com. Prep. Ex. 6 | Com. Prep. Ex. 7 | Com. Prep. Ex. 8 | Com. Prep. Ex. 9 |
|---|---|---|---|
| M | — | B | — |

Compatibility Test

The compatibility test was carried out on the hydroxyl compounds obtained in the Preparation Examples and the Comparative Examples with polyamide resins as a thickner. As the polyamide resins, use was made of amide-terminated polyamide (Sylvaclear A200V from Arizona CHEMICAL, US) and ester-terminated polyamide (Uniclear100VG from Arizona CHEMICAL, US). The hydroxyl compound of, 95% by mass and the polyamide resin of 5% by mass were dissolved in a water bath at a temperature of from 90 to 100 degrees C. for 60 min. under stirring, then cooled to 50 degrees C. under stirring, and kept in a temperature-controlled room at 25 degrees C. One week later, the state was evaluated visually. One with high transparency was rated as "G"; turbidity or slight separation, as "M"; and complete separation, as "B". The results are indicated in Table 4.

TABLE 4

| Compatibility with amide-terminated polyamide resins | | | | | | |
|---|---|---|---|---|---|---|
| | Prep. Ex. 1 | Prep. Ex. 2 | Prep. Ex. 3 | Prep. Ex. 4 | Prep. Ex. 5 | Prep. Ex. 6 |
| Rating | G | G | G | G | G | G |
| | Prep. Ex. 7 | Com. Prep. Ex. 1 | Com. Prep. Ex. 2 | Com. Prep. Ex. 3 | Com. Prep. Ex. 4 | Com. Prep. Ex. 5 |
| Rating | G | M | G | B | B | B |
| | Com. Prep. Ex. 6 | Com. Prep. Ex. 7 | Com. Prep. Ex. 8 | Com. Prep. Ex. 9 | | |
| Rating | M | — | M | — | | |

As seen from Tables 2 to 4, the hydroxyl compounds to be used in the cosmetics of the present invention demonstrated good compatibility with various oily bases, a good water-holding property, and good compatibility with polyamide resins.

Meanwhile, the hydroxyl compound of Comparative Preparation Example 1 demonstrated relatively good compatibility with various oily bases, but did not show compatibility with pentaerythrityl tetraisostearate. The water-holding property and the compatibility with polyamide resins were worse. The hydroxyl compound of Comparative Preparation Example 2 was good in water-holding property and compatibility with polyamide resins, but worse in compatibility with oil bases. The hydroxyl compounds of Comparative Preparation Examples 4 and 8 were relatively good in compatibility with oily bases, but worse in water-holding property and compatibility with amide resins. The hydroxyl compounds of Comparative Preparation Examples 3, 5, and 6 were all worse in compatibility with oily bases, water-holding property, and compatibility with polyamide resins.

EXAMPLES

The ingredients used in the following Examples and Comparative Examples were as indicated in Table 5.

TABLE 5

| Trademark | Chemical name | Manufacturer |
|---|---|---|
| DPG-RF | DPG | Kuraray Co., Ltd. |
| Olive squalane | Squalane | Kokyu Alcohol Kogyo Co., Ltd. |
| ICEH | Hexyldecyl ethylhexanoate | Kokyu Alcohol Kogyo Co., Ltd. |
| Behenyl alcohol 65 | Behenyl alcohol | Kokyu Alcohol Kogyo Co., Ltd. |
| NIKKOL DGMS | Polyglyceryl-2 stearate | Nikko Chemicals Co., Ltd. |
| NIKKOL Decaglyn 1-SV | Polyglyceryl-10 stearate | Nikko Chemicals Co., Ltd. |
| Risorex PGL101 | Polyglyceryl-10 laurate | Kokyu Alcohol Kogyo Co., Ltd. |
| NIKKOL SS-10 | Sorbitan stearate | Nikko Chemicals Co., Ltd. |
| TSF451-100A | Dimethicone | Toshiba Silicones |
| Diol PD | Pentylene glycol | Kokyu Alcohol Kogyo Co., Ltd. |
| Triol VE | Glycerin | Kokyu Alcohol Kogyo Co., Ltd. |
| Amisoft HS-11(P) | Sodium Stearoyl Glutamate* | Ajinomoto |
| KELTROL T | Xanthan gum | Sansho Co., Ltd. |
| Carbopol ETD2050 | Carbomer | Nikko Chemicals Co., Ltd. |
| Risorex PGIS21 | Polyglyceryl-2 isostearate | Kokyu Alcohol Kogyo Co., Ltd. |
| Risorex PGIS32 | Polyglyceryl-3 diisostearate | Kokyu Alcohol Kogyo Co., Ltd. |

TABLE 5-continued

| Trademark | Chemical name | Manufacturer |
|---|---|---|
| Risorex PGIS101 | Polyglyceryl-10 isostearate | Kokyu Alcohol Kogyo Co., Ltd. |
| KAK NDO | Neopentyl glycol diethylhexanoate | Kokyu Alcohol Kogyo Co., Ltd. |
| Rheopear I TT | Dextrin palmitate/ethylhexanoate | Chiba Seifun |
| Purified microcrysatlline wax | Microcrysatlline wax | Nikko Rica |
| MT-100TV | Titanium oxide, alminium hydroxide, stearic acid | Tayca Corporation |
| Catinal HC-100 | Polyquatanium-10 | Toho Chemical Industry Co, Ltd. |
| Obazolin LB-SF | Lauryl betaine, water | Toho Chemical Industry Co, Ltd. |
| Amisole CDE | Cocamide DEA | Kawaken Fine Chemicals Co., Ltd. |
| Elfacos GT 282S | Ceteareth-60 myristil glycol | Lion Corporation |
| Neoscoap CN-30SF | Sodium methylcocoyl taurate, water | Toho Chemical Industry Co, Ltd. |
| Alscoap TH-330 | Sodium laureth sulfate, Water | Toho Chemical Industry Co, Ltd. |
| GENAPOL PMS | Glycol distearate | Clariant (Japan) K. K. |
| Catinal MPAS | Stearamide propyl dimethylamine | Toho Chemical Industry Co, Ltd. |
| BY22-029 | Highly polymerized methyl polysiloxane (1) | Dow Corning Toray Silicone. Co., Ltd. |
| Risorex PGIS23 | Polyglyceyl-2 triisostearate | Kokyu Alcohol Kogyo Co., Ltd. |
| Poem V-100 | Glyceryl stearate | Riken Vitamin Co., Ltd. |
| AMREPS PC | Cetyl palmitate | Kokyu Alcohol Kogyo Co., Ltd. |
| CETOSTEARYL ALCOHOL | Cetostearyl alcohol | Kokyu Alcohol Kogyo Co., Ltd. |
| Arquad 22-80 | Behentrimonium chloride | Lion Corporation |
| Cation DS | Quatanium-18 | Sayo Chemical Industries, Ltd. |
| EMALEX 603 | Steareth-3 | Nihon-Emulsion Co., Ltd. |
| EMALEX 606 | Steareth-6 | Nihon-Emulsion Co., Ltd. |
| Metolose 60SH-4000 | Hydroxypropyl methyl cellulose | Shin-Etsu Chemical Co., Ltd |
| NIPAGIN M | Methyl paraben | Clariant (Japan) K. K. |
| Hisolve EPH | Phenoxy ethanol | Toho Chemical Industry Co, Ltd. |
| Lipoflow MN | Polyquatanium-7 | Lion Corporation |
| Promois silk-1000Q | Silk hydrolysate | Seiwa Kasei Co., Ltd. |
| ECO OIL RS | Jojoba oil | Kokyu Alcohol Kogyo Co., Ltd. |
| RISOCAST MIS | Hydrogenated castor oil isostearate | Kokyu Alcohol Kogyo Co., Ltd. |
| Ceresin B | Ceresin | Nikko Rica |
| CANDELILLA WAX SP-75 | Candelilla wax | STRAHL & PITSCH INC. |
| SH245 | Cyclomethicone | Dow Corning Toray Silicone. Co., Ltd. |
| NEOLIGHT200P | Octyldodecyl neopentanoate | Kokyu Alcohol Kogyo Co., Ltd. |
| KAK TTI | Trimethylolpropane triisostearate | Kokyu Alcohol Kogyo Co., Ltd. |
| Ceresin SP1020 | Ceresin | Ina Trading Shokai* |
| Polywax 500 | Polyethylene | BAKER PETROLITE |
| HAIMALATE DIS | Diisostearyl malate | Kokyu Alcohol Kogyo Co., Ltd. |
| E-mix-D | Tocopherol | Eisai Co., Ltd. |
| NPDC | Neopentylglycol dicaprate | Kokyu Alcohol Kogyo Co., Ltd. |
| KAK PTI | Pentaerythrityl tetraisostearate | Kokyu Alcohol Kogyo Co., Ltd. |
| Tipaque CR-30 | Titanium oxide | Ishihara Sangyo Kaisha, Ltd. |
| Bengara | Iron oxide | KISHI KASEI CO., LTD. |
| Red No. 226 | Red 226 | KISHI KASEI CO., LTD. |
| Timiron MP-115 | Titanium oxide, mica | Merck Ltd, Japan |
| Sylvaclear A200V | Amide terminated polyamide | US Arizona CHEMICAL |
| KAK 139 | Isotridecyl isononanoate | Kokyu Alcohol Kogyo Co., Ltd. |
| Prominence RYH | Synthetic Fluorphlogopite, titanium oxide, iron oxide | Topy Industries, Ltd. |
| Red No. 201 | Red 201 | KISHI KASEI CO., LTD. |
| Yellow No. 5 | Yellow 5 | KISHI KASEI CO., LTD. |
| Uniclear 100VG | Ester terminated polyamide | US Arizona CHEMICAL |
| KAK PTO | Pentaerythrityl tetraethylhexanoate | Kokyu Alcohol Kogyo Co., Ltd. |
| KAK TTO | Trimethlolpropane triethylhexanoate | Kokyu Alcohol Kogyo Co., Ltd. |
| DC glitter gold | (PET/Al/epoxy resin)laminate, iiron oxide | Daiya Chemco* |
| CEH | Cetyl ethylhexanoate | Kokyu Alcohol Kogyo Co., Ltd. |
| Red No. 202 | Red 202 | KISHI KASEI CO., LTD. |
| Blue No. 1 | Blue 1 | KISHI KASEI CO., LTD. |
| J-68-NHS | Talc | US Cosmetics |
| NHS-TRI-77891 | Titanium oxide | US Cosmetics |
| NHS-Y-77492 | Iron oxide (yellow iron oxide) | US Cosmetics |
| NHS-R-77491 | Iron oxide (red iron oxide) | US Cosmetics |
| NHS-B-77499 | Iron oxide (black iron oxide) | US Cosmetics |
| ESCALOL 557 | Octyl methoxycinnamate | ISP Technologies |

*Phonetic translation

Practical properties and storage stability of the cosmetics were evaluated in the following manner.

[Practical Properties]

Subjects were ten males and ten females. Each subject used the cosmetics obtained from the Example and Comparative Example five times in 10 days to evaluate their oily feeling, affinity, and emollient property. Each evaluation item was rated on in six classes and given a score "5" for the best and to "0" for the worst. The evaluation was made on the averaged score among the whole subjects. The evaluation "G" was assigned for an average score of 3.5 to 5.0; "M" for an average score of 2.5 to 3.4; and "B" for an average score of 0 to 2.4.

[Storage Stability]

The cosmetics obtained in the Examples and the Comparative Examples were stored at 45 degrees C. in a temperature-controlled room for three months. Then, the compositions were stored at −5 degrees C. for one day, and then at 45 degrees C. for two days in a temperature controlled room, which operation was repeated 5 times. For solid cosmetics perspiration and discoloration were evaluated. For emulsified cosmetics emulsion state, i.e. occurrence of separation were evaluated. For liquid cosmetics appearance such as separation and discoloration were evaluated. When no abnormality was observed, the cosmetic was evaluated as good and given the rate "G". When minor abnormality was observed and, however, it was thought that the cosmetic had practically no problems, the cosmetic was rated as "M". When abnormality was observed, the cosmetic was evaluated as bad, and given "B".

[Safety to Skin]

Subjects were twenty people, i.e. ten males and ten females. 0.05 g of each cosmetic obtained in the Examples or the Comparative Examples was applied to a circular patch with cotton lint of 1.0 cm diameter, which patch was applied to the forearm flexor of each subject and left for 24 hours. The patch was removed and the skin was examined 1 hour later and 24 hours later to rate the skin conditions of each subject according to the following criteria. When the results 1 hour later and 24 hours later were different, the stronger response was used for rating. When the 20 subjects exhibited (−), the rating was "G"; when 1 to 2 subjects exhibited (±) and the other subjects exhibited (−), the rating was "M"; and when three or more subjects exhibited (±) and the other subjects exhibited (−) or when one or more subjects exhibited (+) to (+++), the rating was "B". For a shampoo, rinse, and hair treatment, aqueous 5% solutions were used.

| Rating Criteria | |
| --- | --- |
| Skin Conditions | Rating |
| Erythema, edema, and blister: | (+++) |
| Erythema, and edema: | (++) |
| Erythema: | (+) |
| Slight erythma: | (±) |
| No erythema, and no edema: | (−) |

Example 1 Preparation of a Skin Cream of O/W Type

Each of the following compositions A and B indicated in Table 6 was separately dissolved homogeneously at a temperature of from 75 degrees C. to 80 degrees C. Then the Composition B was added to Composition A under stirring and then emulsified with a homomixer. The obtained mixture was cooled under stirring to 30 degrees C. to prepare a skin cream.

TABLE 6

| | | Ingredient | % by mass |
| --- | --- | --- | --- |
| (A) | 1 | DPG | 10.00 |
| | 2 | Squalane | 8.00 |
| | 3 | Hydroxyl compound of Prep. Ex. 5 | 2.00 |
| | 4 | Hexyldecyl ethylhexanoate | 7.00 |
| | 5 | Behenyl alcohol | 1.50 |
| | 6 | Polyglyceryl-2 stearate | 1.50 |
| | 7 | Polyglyceryl-10 stearate | 1.50 |
| | 8 | Polyglyceryl-10 laurate | 0.50 |
| | 9 | Sorbitan stearate | 1.00 |
| | 10 | Dimethicone | 0.30 |
| | 11 | Pentylene glycol | 2.50 |
| (B) | 12 | Glycerin | 5.00 |
| | 13 | Sodium stearoyl glutamate | 0.40 |
| | 14 | Xanthan gum | 0.20 |
| | 15 | Carbomer | 0.20 |
| | 16 | Purified water | Balance |
| | 17 | Potassium hydroxide | 0.05 |

Comparative Example 1 Preparation of a Skin Cream of O/W Type

The procedures of Example 1 were repeated to prepare a skin cream, except that the hydroxyl compound of Comparative Preparation Example 2 was used instead of that of Preparation Example 5.

| | Practical properties | Storage stability | Safety to skin |
| --- | --- | --- | --- |
| Example 1 | G | G | G |
| Comparative Example 1 | M | M | G |

The skin cream of Example 1 provided appropriate oily feeling and exhibited the good evaluation. The skin cream of Comparative Example 1 had sticky feeling and the worse storage stability.

Example 2 Preparation of an Emollient Cream of W/O Type

Each of the Compositions A, B, and C indicated in Table 7 was separately dissolved homogeneously at a temperature of from 75 to 80 degrees C. Then Composition B was added to Composition A under stirring. To the obtained mixture in gel-like state was slowly added Composition C under stirring and then emulsified with a homomixer. Then the mixture was cooled under stirring to 30 degrees C. to obtain an emollient cream.

TABLE 7

| | | Ingredient | % by mass |
| --- | --- | --- | --- |
| (A) | 1 | Polyglyceryl-2 isostearate | 1.20 |
| | 2 | Polyglyceryl-3 diisostearate | 2.40 |
| | 3 | Polyglyceryl-10 isostearate | 1.60 |
| | 4 | Squalane | 8.00 |
| | 5 | Neopentylglycol diethylhexanoate | 7.00 |
| | 6 | Hydroxyl compound of Prep. Ex. 6 | 2.00 |
| | 7 | Dextrin palmitate/ethylhexanoate | 0.50 |
| | 8 | Microcrystalline wax | 4.00 |
| (B) | 9 | Glycerin | 8.00 |
| | 10 | Purified water | 3.00 |
| (C) | 11 | Pentylene glycol | 3.00 |
| | 12 | Purified water | Balance |

Comparative Example 2 Preparation of an Emollient Cream of W/O Type

An emollient cream was prepared in the same manner as in Example 2, except that the hydroxyl compound of Comparative Preparation Example 1 was used instead of that of Preparation Example 6.

| | Practical properties | Storage stability | Safety to skin |
| --- | --- | --- | --- |
| Example 2 | G | G | G |
| Comparative Example 2 | M | B | G |

The emollient cream of Example 2 provided appropriate oily feeling and exhibited the good evaluation. The emollient cream of Comparative Example 2 had sticky feeling and the very poor storage stability.

Example 3 Preparation of a Suncream of W/O Type

First, Ingredient 9 indicated in Table 8 was dispersed in Ingredients 5 and 6 with a homomixer. Each Composition A, B, and C was separately dissolved homogeneously at a temperature of from 75 degrees C. to 80 degrees C. Then Composition B was added to Composition A under stirring. To the obtained mixture in a gel-like state was slowly added Composition C and then emulsified with a homomixer. Then the mixture was cooled to 30 degrees C. under stirring to obtain a suncream.

TABLE 8

|     |    | Ingredient | % by mass |
|-----|----|------------|-----------|
| (A) | 1  | Polyglyceryl-2 isostearate | 1.20 |
|     | 2  | Polyglyceryl-3 diisostearate | 2.50 |
|     | 3  | Polyglyceryl-10 isostearate | 1.20 |
|     | 4  | Polyglyceryl-10 laurate | 0.30 |
|     | 5  | Squalane | 8.00 |
|     | 6  | Hexyldecyl ethylhexanoate | 8.00 |
|     | 7  | Hydroxyl compound of Prep. Ex. 4 | 1.00 |
|     | 8  | Dextrin palmitate/ethylhexanoate | 0.50 |
|     | 9  | Titanium oxide fine particles treated with aluminum isostearate [Tradename: MT-100TV] | 9.00 |
|     | 10 | Microcrystalline wax | 1.00 |
| (B) | 11 | Glycerin | 10.00 |
|     | 12 | Purified water | 4.00 |
| (C) | 13 | Pentylene glycol | 3.00 |
|     | 14 | Purified water | Balance |

Comparative Example 3 Preparation of a Suncream of W/O Type

A suncream was prepared in the same manner as in Example 31 except that the hydroxyl compound of Comparative Preparation Example 1 was used instead of that of Preparation Example 4.

|  | Practical properties | Storage stability | Safety to skin |
|---|---|---|---|
| Example 3 | G | G | G |
| Comparative Example 3 | M | M | G |

The suncream of W/O type of Example 3 was good in spreadability and gave a refreshing feel on application. The suncream of Comparative Example 3 was bad in spreadability and had drawbacks such as sticky feeling.

Example 4 Preparation of a Conditioning Shampoo

The hydroxyl compound of Preparation Example 1 and Ingredients 3 and 4 described in Table 9 were heat dissolved beforehand. Then, all of the ingredients were homogeneously dissolved at a temperature of from 75 degrees C. to 80 degrees C. and then cooled to 30 degrees C. according to the general method to obtain a conditioning shampoo.

TABLE 9

|    | Ingredient | % by mass |
|----|------------|-----------|
| 1  | Polyquatanium-10 | 1.00 |
| 2  | Purified water | Balance |
| 3  | Polyglyceryl-10 isostearate | 1.5 |
| 4  | Polyglyceryl-10 laurate | 1.0 |

TABLE 9-continued

|    | Ingredient | % by mass |
|----|------------|-----------|
| 5  | Hydroxyl compound of Prep. Ex. 1 | 0.5 |
| 6  | Lauryl betaine (aq. 30% solution) | 10.0 |
| 7  | Cocamide DEA | 4.0 |
| 8  | Lauryldimethyl aminoxide(aq. 30% solution) | 1.0 |
| 9  | Ceteareth-60 myristilglycol | 2.0 |
| 10 | Sodium methylcocoyltaurate(aq.30% solution) | 27.0 |
| 11 | Sodium laureth sulfate (aq. 30% solution) | 23.0 |
| 12 | Glycol distearate | 2.0 |
| 13 | Pentylene glycol | 3.0 |
| 14 | Stearamide propyl dimethylamine | 0.3 |
| 15 | Citric acid (aq.10% solution) | 3.5 |
| 16 | Highly polymerized methyl polysiloxane (1) | 0.3 |

Comparative Example 4 Preparation of a Conditioning Shampoo

A conditioning shampoo was prepared in the same manner as in Example 4, except that the hydroxyl compound of Comparative Preparation Example 5 was used instead of that of Preparation Example 1.

|  | Practical stability | Storage stability | Safety to skin |
|---|---|---|---|
| Example 4 | G | G | G |
| Comparative Example 4 | M | B | G |

The conditioning shampoo of Example 4 provided appropriate oily feeling and no stiffness to hair after shampooing. Meanwhile, with the conditioning shampoo of Comparative Example 4, the remaining oil base exhibited high affinity to give uncomfortable feeling on the hair.

Example 5 Preparation of a Rinse

Each of Compositions A, B, and C indicated in Table 10 was separately dissolved homogeneously at a temperature of from 75 degrees C. to 80 degrees C. Then Composition B was added to Composition A under stirring and then the mixture, Compositions A+B, was emulsified with a homomixer. Further, Composition C was added to the mixture of Compositions A+B under stirring and the obtained mixture was cooled to 30 degrees under stirring to prepare a rinse.

TABLE 10

|     |    | Ingredient | % by mass |
|-----|----|------------|-----------|
| (A) | 1  | Neopentyl glycol diethylhexanoate | 1.00 |
|     | 2  | Polyglyceryl-10 laurate | 0.50 |
|     | 3  | Polyglyceryl-2 triisostearate | 1.00 |
|     | 4  | Hydroxyl compound of Prep. Ex. 2 | 1.00 |
|     | 5  | Glyceryl stearate | 1.00 |
|     | 6  | Cetyl palmitate | 0.50 |
|     | 7  | Cetostearyl alcohol | 1.60 |
|     | 8  | Behenyl alcohol | 0.40 |
|     | 9  | Behentrimonium chloride | 2.70 |
|     | 10 | Quatanium-18 | 0.30 |
|     | 11 | DPG | 2.00 |
|     | 12 | Steareth-3 | 1.30 |
|     | 13 | Steareth-6 | 1.80 |

TABLE 10-continued

| | | Ingredient | % by mass |
|---|---|---|---|
| (B) | 14 | Hydroxypropyl methyl cellulose | 0.40 |
| | 15 | DPG | 1.25 |
| | 16 | Methyl paraben | 0.11 |
| | 17 | Phenoxy ethanol | 0.50 |
| | 18 | Polyquatanium-7 | 1.00 |
| | 19 | Purified water | Balance |
| | 20 | Silk hydrolysate | 0.01 |
| (C) | 21 | Highly polymerized methyl polysiloxane (1) | 0.30 |
| | 22 | Citric acid (aqueous 10% solution) | 0.10 |
| | 23 | Sodium citrate(aqueous 10% solution) | 0.40 |

Comparative Example 5 Preparation of a Rinse

A rinse was prepared according to the same manner as Example 5, except that the hydroxyl compound of Comparative Preparation Example 6 was used instead of that of Preparation Example 2.

| | Practical stability | Storage stability | Safety to skin |
|---|---|---|---|
| Example 5 | G | G | G |
| Comparative Example 5 | B | M | G |

The rinse of Example 5 provided appropriate oily feeling and no stiffness to hair after shampooing. Meanwhile, the rinse of Comparative Example 5 exhibited such a drawback that the hair was uneasy to comb and hair got stuck on a comb.

Example 6 Preparation of a Hair Treatment

Each of Compositions A, B, and C indicated in Table 11 was separately dissolved homogeneously at a temperature of from 75 degrees C. to 80 degrees C. Then Composition B was added to Composition A under stirring and then the mixture, Compositions A+B, was emulsified with a homomixer. Further, Composition C was added to the mixture of Compositions A+B and the obtained mixture was cooled to 30 degrees under stirring to prepare a hair treatment.

TABLE 11

| | | Ingredient | % by mass |
|---|---|---|---|
| (A) | 1 | Jojoba oil | 1.00 |
| | 2 | Neopentyl glycol diethylhexanoate | 3.00 |
| | 3 | Polyglyceryl-10 laurate | 0.50 |
| | 4 | Polyglyceryl-2 triisostearate | 2.00 |
| | 5 | Hydrogenated castor oil isostearate | 1.00 |
| | 6 | Hydroxyl compound of Prep. Ex. 3 | 2.00 |
| | 7 | Glyceryl stearate | 1.00 |
| | 8 | Cetyl palmitate | 0.50 |
| | 9 | Cetostearyl alcohol | 4.40 |
| | 10 | Behenyl alcohol | 1.10 |
| | 11 | Behentrimonium chloride | 2.70 |
| | 12 | Quatanium-18 | 0.40 |
| | 13 | DPG | 2.00 |
| | 14 | Steareth-3 | 1.50 |
| | 15 | Steareth-6 | 1.50 |
| | 16 | Dimethicone | 1.00 |
| (B) | 17 | Hydroxypropyl methyl cellulose | 0.30 |
| | 18 | Pentylene glycol | 3.00 |
| | 19 | Polyquatanium-7 | 1.00 |
| | 20 | Purified water | Balance |
| | 21 | Silk hydrolysate | 0.01 |
| (C) | 22 | Highly polymerized methyl polysiloxane (1) | 1.00 |

Comparative Example 6 Preparation of a Hair Treatment

A hair treatment was prepared according to the same manner as Example 6, except that the hydroxyl compound of Comparative Preparation Example 8 was used instead of that of Preparation Example 3.

| | Practical stability | Storage stability | Safety to skin |
|---|---|---|---|
| Example 6 | G | G | G |
| Comparative Example 6 | M | M | G |

The hair treatment of Example 6 provided appropriate oily feeling and no stiffness to the hair after shampooing. Meanwhile, the hair treatment of Comparative Preparation Example 6 did not provide oily feeling to hair after shampooing and was worse in storage stability.

Example 7 Preparation of a Hair Wax

Each of Compositions A and B indicated in Table 12 was separately dissolved homogeneously at a temperature of from 75 to 80 degrees C. Then Composition A was added to Composition B under stirring and emulsified with a homomixer. Then the mixture was cooled to 30 degrees C. under stirring to prepare a hair wax.

TABLE 12

| | | Ingredient | % by mass |
|---|---|---|---|
| (A) | 1 | Hydroxyl compound of Prep. Ex. 4 | 3.0 |
| | 2 | Neopentyl glycol diethylhexanoate | 5.1 |
| | 3 | Ceresin [Tradename: Ceresin B] | 3.9 |
| | 4 | Candelilla wax | 5.2 |
| | 5 | Polyglyceryl-2 isostearate | 2.2 |
| | 6 | Polyglyceryl-10 isostearate | 3.8 |
| | 7 | Dimethicone | 2.0 |
| | 8 | Cyclomethicone | 1.0 |
| | 9 | Behenyl alcohol | 2.7 |
| | 10 | Glyceryl stearate | 2.7 |
| | 11 | Pentylene glycol | 3.0 |
| | 12 | Steareth-6 | 1.0 |
| (B) | 13 | Sodium stearoyl glutamate | 0.6 |
| | 14 | Hydroxypropyl methyl cellulose | 0.6 |
| | 15 | Purified water | Balance |

Comparative Example 7 Preparation of a Hair Wax

A hair wax was prepared according to the same manner as in Example 7, except that the hydroxyl compound of Comparative Preparation Example 4 was used instead of that of Preparation Example 4.

| | Practical stability | Storage stability | Safety to skin |
|---|---|---|---|
| Example 7 | G | G | G |
| Comparative Example 7 | M | M | G |

The hair wax of Example 7 provided appropriate oily feeling to hair after shampooing and was highly effective in setting hair. Meanwhile, the hair wax of Comparative Preparation Example 7 exhibited such a drawback that it was sticky on application and the hair treated with the wax was uneasy to comb.

Example 8 Preparation of a Lip Cream

All of the ingredients indicated in Table 13 were dissolved homogeneously at a temperature of from 95 degrees C. to 100 degrees C. and deaerated. Then, the mixture was cast into an appropriate mould and cooled to prepare a lip cream.

TABLE 13

| | Ingredient | % by mass |
|---|---|---|
| 1 | Hydroxyl compound of Prep. Ex. 5 | 17.00 |
| 2 | Octyldodecyl neopentanoate | 24.00 |
| 3 | Trimethylolpropane triisostearate | 22.99 |
| 4 | Microcrystalline wax (mp: 78° C.) | 4.00 |
| 5 | Ceresin (mp: 73-76° C.) | 6.00 |
| 6 | Polyethylene (mp: 88° C.) | 5.00 |
| 7 | Diisostearyl malate | 15.00 |
| 8 | Polyglyceryl-2 triisostearate | 6.00 |
| 9 | d-delta-tocopherol | 0.01 |

Comparative Example 8 Preparation of a Lip Cream

A lip cream was prepared according to the same manner as in Example 8, except that the hydroxyl compound of Comparative Preparation Example 1 was used instead of that of Preparation Example 5.

| | Practical stability | Storage stability | Safety to skin |
|---|---|---|---|
| Example 8 | G | G | G |
| Comparative Example 8 | M | B | G |

The lip cream of Example 8 was good in spreadability and gave smooth touch on application. It also showed only a little change in hardness when stored at temperatures of 5 degrees C., 25 degrees C., and 35 degrees C. That is, the hardness was 0.55 N at 5 degrees C.; 0.30 N at 25 degrees C.; and 0.17 N at 35 degrees C. Thus the lip cream kept its shape. Meanwhile, the lip cream of Comparative Example 8 exhibited perspiration and poor storage stability. The comparative lip cream exhibited a large change in hardness with temperature change. That is, the hardness was 0.65 N at 5 degrees C., 0.22 N at 25 degrees C.; and 0.08 N at 35 degrees. The lip cream had drawbacks such as bad spreadability and sticky feeling on application.

The hardness was determined with EZ-Test-20N from Shimadzu. With a needle diameter of 1.0 mm and a test speed of 10 mm/min, the stress in N was determined at a needle penetration depth of 10 mm. The maximum stress was taken as hardness.

Example 9 Preparation of a Lip Stick

Ingredients 7 and Ingredients 9 to 13 indicated in Table 14 were homogeneously dispersed with a three-roller kneader beforehand. All of the remaining ingredients and the aforementioned dispersion were homogeneously dissolved at a temperature of from 95 to 100 degrees C. and deaerated. Then the mixture was cast in an appropriate mould and cooled to obtain a lip stick

TABLE 14

| | Ingredient | % by mass |
|---|---|---|
| 1 | Hydroxyl compound of Prep. Ex. 1 | 18.00 |
| 2 | Neopentylglycol dicaprate | 22.79 |
| 3 | Pentaerythrityl tetraisostearate | 19.00 |
| 4 | Microcrystalline wax (mp: 78° C.) | 5.50 |
| 5 | Candelilla wax (mp: 68-74° C.) | 5.80 |
| 6 | Polyethylene (mp: 88° C.) | 5.70 |
| 7 | Diisostearyl malate | 10.00 |
| 8 | Polyglyceryl-2 triisostearate | 6.00 |
| 9 | Titanium oxide [Tradename: Tipaque CR-30] | 1.00 |
| 10 | Iron oxide [bengara] | 1.20 |
| 11 | Red No. 226 | 0.20 |
| 12 | Titanium oxide, mica [mica coated with titanium oxide] | 4.80 |
| 13 | d-delta-tocopherol | 0.01 |

Comparative Example 9 Preparation of a Lip Stick

A lip stick was prepared in the same manner as in Example 9, except that the hydroxyl compound of Comparative Preparation Example 2 was used instead of the hydroxyl compound of Preparation Example 1.

| | Practical properties | Storage stability | Safety to skin |
|---|---|---|---|
| Example 9 | G | G | G |
| Comparative Example 9 | B | M | G |

The lip stick of Example 9 was good in spreadability on application. It also showed only a little change in hardness when stored at temperatures of 5 degrees C., 25 degrees C., and 35 degrees C. That is, the hardness was 0.57 N at 5 degrees C.; 0.31 N at 25 degrees C.; and 0.15 N at 35 degrees C. Thus the lip cream kept its shape. Meanwhile, the lip cream of Comparative Example 9 was sticky and poor in the practical properties. The comparative lip cream exhibited a large change in hardness with temperature change. That is, the hardness was 0.63 N at 5 degrees C., 0.21 N at 25 degrees C.; and 0.06 N at 35 degrees.

Example 10 Preparation of a Pasty Lip Gloss

Ingredients 1 to 3 and Ingredient 5 indicated in Table 15 were homogeneously dissolved. Meanwhile, Ingredients 6 to 10 were homogeneously dispersed in Ingredient 4 at the same temperature. Then all of these ingredients were homogeneously mixed and then cooled to 30 degrees C. to prepare a pasty lip gloss.

TABLE 15

| | Ingredient | % by mass |
|---|---|---|
| 1 | Hydroxyl compound of Prep. Ex. 7 | 40.00 |
| 2 | Pentaerythrityl tetraisostearate | 35.00 |
| 3 | Cetyl ethylhexanoate | 3.00 |
| 4 | Diisostearyl malate | 13.77 |
| 5 | Polyglyceryl-2 triisostearate | 5.00 |
| 6 | Titanium oxide | 1.50 |
| 7 | Iron oxide [bengara] | 1.50 |
| 8 | Red No. 201 | 0.10 |
| 9 | Red No. 202 | 0.08 |
| 10 | Blue No. 1 | 0.05 |

Comparative Example 10 Preparation of a Pasty Lip Gloss

A lip stick was prepared in the same manner as in Example 10, except that the hydroxyl compound of Comparative Preparation Example 3 was used instead of the hydroxyl compound of Preparation Example 7.

|  | Practical stability | Storage stability | Safety to skin |
| --- | --- | --- | --- |
| Example 10 | G | G | G |
| Comparative Example 10 | M | M | G |

The pasty lip gloss of Example 10 provided lips with appropriate covering feeling and had good spreadability and little sticky feeling. Meanwhile, the pasty lip gloss of Comparative Example 10 had strong sticky feeling and poor practical properties.

Example 11 Preparation of a Lip Gloss of Pallet Type

Ingredients 1 to 4 and Ingredient 6 indicated in Table 16 were homogeneously dissolved at a temperature of from 90 to 100 degrees C. Meanwhile ingredients 8 to 9 were dispersed in ingredient 5 at the same temperature. Then all of these ingredients were homogeneously mixed and Ingredient 7 was added and mixed homogeneously. Then the mixture was cast in a plate-like mould and cooled to a temperature of 30 degrees C. to prepare a lip gloss.

TABLE 16

| Ingredient | % by mass |
| --- | --- |
| 1 Hydroxyl compound of Prep. Ex. 2 | 25.00 |
| 2 Amide terminated polyamide | 6.00 |
| 3 Hexyldecyl ethylhexanoate | 36.50 |
| 4 Isotridecyl isononanoate | 8.00 |
| 5 Diisostearyl malate | 15.00 |
| 6 Polyglyceryl-2 triisostearate | 6.00 |
| 7 Synthetic Fluorphlogopite, titanium oxide, iron oxide | 3.00 |
| 8 Red No. 201 | 0.20 |
| 9 Yellow No. 5 | 0.30 |

Comparative Example 11 Preparation of a Lip Gloss of Pallet Type

A lip stick was prepared in the same manner as in Example 11, except that the hydroxyl compound of Comparative Preparation Example 8 was used instead of the hydroxyl compound of Preparation Example 2.

|  | Practical stability | Storage stability | Safety to skin |
| --- | --- | --- | --- |
| Example 11 | G | G | G |
| Comparative Example 11 | M | B | G |

The lip gloss of Example 11 provided lips with appropriate covering feeling and had good spreadability and little sticky feeling. Meanwhile, the lip gloss of Comparative Example 11 had little covering feeling on application and poor practical properties.

Example 12 Preparation of a Lip Gloss of Pallet Type

Ingredients 1 to 4 and ingredient 6 indicated in Table 17 were homogeneously dissolved at a temperature of from 90 to 100 degrees C. Meanwhile Ingredients 8 to 9 were dispersed in Ingredient 5 at the same temperature. Then all of these were mixed homogeneously and Ingredient 7 was added and mixed homogeneously. Then the mixture was cast in a plate-like mould and cooled to a temperature of 30 degrees C. to prepare a lip gloss.

TABLE 17

| Ingredient | % by mass |
| --- | --- |
| 1 Hydroxyl compound of Prep. Ex. 6 | 38.50 |
| 2 Ester terminated polyamide | 4.00 |
| 3 Pentaerythrityl tetraethylhexanoate | 25.00 |
| 4 Trimethlolpropane triethylhexanoate | 10.00 |
| 5 Diisostearyl malate | 12.00 |
| 6 Polyglyceryl-2 triisostearate | 5.00 |
| 7 (PET/Al/epoxy resin) laminate, iron oxide | 5.00 |
| 8 Red No. 201 | 0.20 |
| 9 Yellow No. 5 | 0.30 |

Comparative Example 12 Preparation of a Lip Gloss of Pallet Type

A lip gloss was prepared in the same manner as in Example 12, except that the hydroxyl compound of Comparative Preparation Example 6 was used instead of the hydroxyl compound of Preparation Example 6.

|  | Practical stability | Storage stability | Safety to skin |
| --- | --- | --- | --- |
| Example 12 | G | G | G |
| Comparative Example 12 | M | M | G |

The lip gloss of Example 12 provided lips with appropriate covering feeling and had good spreadability and little sticky feeling. Meanwhile, the lip gloss of Comparative Example 12 had little covering feeling on application and poor practical properties.

Example 13 Preparation of a Foundation

Ingredients 1 to 5 and Ingredients 11 to 12 indicated in Table 18 were homogeneously dissolved at a temperature of 90 degrees C. and Ingredients 6 to 10 were added and dispersed homogeneously under stirring with a homodisper. Then the composition was deaerated and cast in a metal plate to prepare a foundation.

TABLE 18

| Ingredient | % by mass |
| --- | --- |
| 1 Hydroxyl compound of Prep. Ex. 4 | 3.00 |
| 2 Polyethylene wax (mp: 88° C.) | 5.00 |
| 3 Ceresin (mp: 73-76° C.) [Ceresin SP 1020] | 8.00 |
| 4 Hexyldecyl ethylhexanoate | Balance |
| 5 Cyclomethicone | 10.00 |
| 6 Talc | 6.00 |
| 7 Titanium oxide | 10.00 |
| 8 Iron oxide [red iron oxide] | 1.50 |
| 9 Iron oxide [yellow iron oxide] | 3.00 |

TABLE 18-continued

| Ingredient | % by mass |
| --- | --- |
| 10 Iron oxide [black iron oxide] | 1.50 |
| 11 Octyl methoxycinnamate | 2.00 |
| 12 d-delta-tocopherol | 0.05 |

Comparative Example 13 Preparation of a Foundation

A foundation was prepared in the same manner as in Example 13, except that the hydroxyl compound of Comparative Preparation Example 3 was used instead of the hydroxyl compound of Preparation Example 4.

| | Practical stability | Storage stability | Safety to skin |
| --- | --- | --- | --- |
| Example 13 | G | G | G |
| Comparative Example 13 | M | M | G |

The foundation of Example 13 was less sticky to skin on application and good in practical properties. Meanwhile, the foundation of Comparative Example 13 had strong sticky feeling on application and poor practical properties.

INDUSTRIAL APPLICABILITY

The cosmetics comprising the hydroxyl compounds of the present invention may be used in, for instance, O/W type creams, W/O type creams, sun care creams, shampoos, rinses, hair treatments, hair waxes, lip creams, lip sticks, pasty lip glosses, solid lip glosses, and foundations.

The invention claimed is:

1. A cosmetic comprising a hydroxyl compound obtained by reacting a glycerin mixture consisting essentially of diglycerin with isostearic acid, and then reacting the obtained ester compound with dimer acid, wherein
 a molar ratio among the diglycerin of the glycerin mixture, isostearic acid, and dimer acid is 1.0:1.4 to 1.6:0.5 to 0.8;
 a hydroxyl value of the hydroxyl compound is in a range of from 30 to 80;
 a viscosity at 60 degrees C. of the hydroxyl compound is in a range of from 2,500 to 10,000 mPa·s; and
 a number average molecular weight of the hydroxyl compound is in a range of from 2,000 to 7,000.

2. The cosmetic according to claim 1, wherein the molar ratio among the diglycerin of the glycerin mixture, isostearic acid and dimer acid is 1.0:1.45 to 1.55:0.55 to 0.75.

3. The cosmetic according to claim 1, wherein the molar ratio among the diglycerin of the glycerin mixture, isostearic acid, and dimer acid is 1.0:1.47 to 1.53:0.6 to 0.7.

4. The cosmetic according to claim 1, wherein the hydroxyl value of the hydroxyl compound is in a range of from 40 to 70.

5. The cosmetic according to claim 1, wherein a viscosity at 60 degrees C. of the hydroxyl compound is in a range of from 3,000 to 8,000 mPa·s.

6. The cosmetic according to claim 1, wherein a number average molecular weight of the hydroxyl compound is in a range of from 3,000 to 6,000.

7. A lipstick composition comprising a hydroxyl compound obtained by reacting a glycerin mixture consisting essentially of diglycerin with isostearic acid, and then reacting the obtained ester compound with dimer acid, wherein
 a molar ratio among the diglycerin of the glycerin mixture, isostearic acid, and dimer acid is 1.0:1.4 to 1.6:0.5 to 0.8;
 a hydroxyl value of the hydroxyl compound is in a range of from 30 to 80;
 a viscosity at 60 degrees C. of the hydroxyl compound is in a range of from 2,500 to 10,000 mPa·s; and
 a number average molecular weight of the hydroxyl compound is in a range of from 2,000 to 7,000.

8. The cosmetic according to claim 1, wherein the hydroxyl compound is obtained by reacting a mixture consisting of a glycerin mixture consisting essentially of diglycerin with isostearic acid, and then reacting the obtained ester compound with dimer acid.

9. The cosmetic according to claim 1, wherein a purity of the diglycerin in the glycerin mixture is at least 93.3% by weight.

* * * * *